United States Patent [19]

Brunetta et al.

[11] Patent Number: 4,803,067
[45] Date of Patent: Feb. 7, 1989

[54] COMPOSITIONS FOR COSMETICS AND DERMATOLOGY COMPRISING PERFLUOROPOLYETHERS

[75] Inventors: Fabio Brunetta, Cornuda; Stefano Bader, Melzo; Giovanni Pantini, Milan, all of Italy

[73] Assignee: Ausimont S.p.A., Milan, Italy

[21] Appl. No.: 844,318

[22] Filed: Mar. 26, 1986

[30] Foreign Application Priority Data

Mar. 29, 1985 [IT] Italy ................. 20161 A/85

[51] Int. Cl.$^4$ ............... A61K 7/48; A61K 31/77; C08L 71/02
[52] U.S. Cl. ........................... 424/63; 424/59; 424/64; 514/723; 514/753; 514/772; 514/789; 514/844; 514/845; 514/846; 514/847; 514/873; 514/939; 514/947; 514/944
[58] Field of Search ............ 424/59, 63, 64; 514/715, 759, 844, 845, 846, 847, 873, 937, 938, 941, 944, 947, 722, 723, 743, 744, 772, 789, 939, 940

[56] References Cited

U.S. PATENT DOCUMENTS

| | | |
|---|---|---|
| 3,242,218 | 3/1966 | Miller .................................. 568/615 |
| 3,665,041 | 5/1972 | Sianesi et al. ....................... 568/601 |
| 3,715,378 | 2/1973 | Sianesi et al. ....................... 558/283 |
| 3,810,874 | 5/1974 | Mitsch et al. ......................... 528/70 |
| 3,847,978 | 11/1974 | Sianesi et al. ................... 524/366 X |
| 3,989,843 | 11/1976 | Chabert et al. ................. 514/743 X |
| 4,094,311 | 6/1978 | Hudson .................................. 128/66 |
| 4,523,039 | 6/1985 | Lagow et al. ....................... 568/615 |
| 4,608,392 | 8/1986 | Jacquet et al. ........................ 424/63 |

FOREIGN PATENT DOCUMENTS 196904 10/1986 European Pat. Off. .

OTHER PUBLICATIONS

Bader et al., "Three-Phase Emulsions: Perfluoropolyether-Oil-Water", Nov. 1986, pp. 45–48, Cosmetics & Toiletries, vol. 101.

Primary Examiner—George F. Lesmes
Assistant Examiner—Susan S. Rucker
Attorney, Agent, or Firm—Stevens, Davis, Miller & Mosher

[57] ABSTRACT

Compositions for cosmetics and dermatology comprising a perfluoropolyether liquid dispersed in an oil/water or water/oil emulsion, or in a solid phase suited to form a gel, suspended in an organic liquid phase.

15 Claims, No Drawings

COMPOSITIONS FOR COSMETICS AND DERMATOLOGY COMPRISING PERFLUOROPOLYETHERS

This invention relates to new compositions which are particularly suitable for applications in the field of cosmetics and dermatology, which comprise as the essential component, a perfluoropolyether liquid dispersed in an aqueous or organic phase.

It is well known in the literature how to prepare oil/water emulsions in which the oil consists of a perfluorinated compound. These emulsions were chiefly prepared in order to provide synthetic plasma, exploiting the high solubility of oxygen and of carbon dioxide in the perfluorinated compounds which, therefore, acted as oxygen carriers. The perfluorinated compounds belong to the classes of the perfluorinated cycloalkanes (preferably with two or more condensed rings), of the heterocyclic perfluorinated compounds, and of the perfluorinated amines, while the compounds having the structure of perfluorpolyethers have proved in the past to be little suited to this kind of application.

In preparing these emulsions, two main difficulties were encountered consisting of the choice of an emulsifier effective for the perfluorinated compounds, and in the obtainment of sufficiently stable products. As regards the emulsifiers, the best results were obtained with the so-called pluronic polyols (non-ionic emulsifiers with the chemical structure of polyalkyloxanes and prepared by starting from mixtures of ethylene oxide and propylene oxide in a proper ratio); as an alternative, also perfluorinated emulsifiers were used which, however, were not capable of performing the other functions performed by the pluronic polyols in the synthetic plasma.

The problem of stability was partially solved by using together different types of perfluorinated compounds (the addition of perfluoramines is useful to stabilize the emulsions), however, the emulsions obtained so far had to be preserved under cold conditions. The emulsions and dispersions according to the present invention are prepared by methods well known in the art.

It has now, surprisingly, been found that it is possible to prepare stable dispersions of perfluoropolyether liquids in water or in an organic liquid immiscible with the perfluoropolyether by using, as a dispersant for the perfluorinated liquid, an emulsion of oil-in-water (O/W) or of water-in-oil (W/O), or a solid phase suited to form a gel, suspended in an organic liquid (in the last case, the solid phase is a substance capable of forming a reticular structure by formation of links of the hydrogen-hydrogen type or links by Van der Waal forces).

Thanks to the film-forming characteristics of the perfluoropolyether component, the compositions of the present invention have the property of forming a transparent and water-repellent liquid film endowed, furthermore, with permeability to oxygen and other gases, and which remains on the surface to which it has been applied over relatively long periods of time.

The water-repellency characteristic of the liquid film renders the compositions particularly suitable for applications in the field of water-repellent cosmetics and for high-efficiency applications in the field of skin-conditioning treatments. As compared with cosmetics of the conventional type, water-repellent cosmetics offer the great advantage of retaining the cosmetic effect for long times and of rendering unnecessary the frequent re-touchings which, conversely, are necessary in the case of conventional cosmetics.

In skin-rehydration treatments it is highly desirable to have available stable, cosmetically acceptable (non-oily, non-tacky, etc.) compositions which, besides the property of carrying to the subcutaneous layers, and to make available therein water in such amounts as are sufficient to obtain the desired moistening effect, and are also capable of exerting a "barrier" effect towards the outside, without adversely affecting, however, the skin respiration.

In spite of the fact that the process of skin respiration exhibits several aspects which still have to be clarified, it is certain, however, that the absorption of oxygen and the elimination of carbon dioxide are of essential importance for the health of the skin.

As already mentioned, the compositions of this invention comprise a perfluoropolyether liquid dispersed in an aqueous or organic phase immiscible with said liquid. More particularly, the perfluoropolyether liquid is maintained dispersed (or emulsified) in a liquid phase through an aqueous or organic phase present as an emulsion in the dispersing liquid phase or through a solid phase suited to form a gel, suspended in a liquid organic phase.

The emulsion in which the perfluoropolyether liquid is dispersed is an oil/water emulsion (O/W) or a water/oil emulsion (W/O) of the conventional type, preparable according to per se known techniques. In particular, the oily phase immiscible with water is selected from amongst fatty acid esters, hydrogenated non-hydrogenated vegetable oils, and linear hydrocarbons of different chain lengths, the preferred hydrocarbons containing for example from 14 to 36 carbon atoms.

The emulsifiers are selected as a function of the oily substance; they may be of the anionic, cationic, or non-ionic type.

In the above-cited O/W and W/O emulsions, the perfluoropolyether represents a "third phase". Through observations under the optical microscope on dispersions of perfluoropolyether at 20–30% by weight, it was possible to perceive the perfluoropolyether phase, which appears in the form of droplets of different sizes, some of which have a larger diameter than those of the emulsified phase (inner phase). The microdrops of the perfluoropolyether compound cannot be colored, wherefore they can be distinguished from the drops of the inner phase, which, conversely, can be colored.

The compositions of the present invention therefore consist or consist essentially of at least three phases immiscible with one another, in which the perfluorinated phase is dispersed in the structure of the emulsified oily or aqueous phase.

The perfluoropolyether dispersions are prepared according to various methods. The preferred method consists in dispersing the perfluoropolyether in water or in the dispersing organic phase. This step is carried out in the presence of heat (e.g., at 70°–80° C.) and with the aid of a mixing turbine running at the maximum speed (e.g., 5,000–10,000 rpm).

The inner phase is then added (which may be an aqueous or oil phase) whereafter it is cooled under stirring (in like manner as for the preparation of conventional emulsions).

Conversely, by adopting the technique of adding the perfluoropolyether to the O/W or W/O emulsions when they are already prepared and cooled down, no good dispersion of the perfluoropolyether can be obtained: the droplets have a rather large diameter, higher by 10–20 times that of the microdrops of the inner phase.

The perfluoropolyether for preparing the emulsion or dispersion according to the present invention ranges from 0.05 to 30 parts per 100 parts of the total sum of the other components. Preferably, 0.2 to 5 parts of perfluoropolyether per 100 parts of the total of the other components are used for preparing the dispersions. The parts referred to in the present invention are intended to be by weight.

The compositions so prepared are endowed with a high stability. Accelerated ageing tests by means of thermoregulation at 40° C. alternated with cooling in a refrigerator at 4° C. in alternating cycles of 24 hours each during one week, and allowing them then to stand for 4 months, have proved that the perfluoropolyether does not demix, not even partially.

Centrifugation tests (5000 rpm during 30 minutes) have proved that the dispersions in the W/O or O/W emulsions are stable even under these conditions.

The perfluoropolyethers utilizable in the compositions of the invention are compounds which contain perfluoroalkylene oxide units or perfluoroxetane rings.

In particular, the repeating units are chosen from the following:

(a) $C_2F_4O$ and $CF_2O$ statistically distributed along the chain;

(b) $C_2F_4O$, $C_3F_6O$ and $CFXO$ ($X=F$ or $CF_3$) statistically distributed along the chain;

(c) $C_3F_6O$ and $CFXO$ ($X=F$ or $CF_3$) statistically distributed along the chain;

(d) oxetane rings:

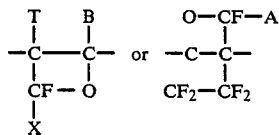

in which A, T and X, equal to or different from each other, are perfluorooxyalkyl, perfluoropolyoxyalkyl or perfluoroalkyl radicals.

The end groups of the perfluoropolyethers may be like or unlike each other and are selected in particular from the radicals F, $CF_3$, $C_2F_5$, $C_3F_7$, Br, or from polar groups containing one or more electron donor atoms or from groups containing one or more aromatic rings, either or not containng heteroatoms, capable of giving rise to coordinated bonds or charge-transfer bonds.

The mean number avergage molecular weight is generally higher than 500 and ranges in particular from 1,000 to 10,000. The viscosity values (cSt at 20° C.) are generally in the range of from 30 to 5,000.

Particular examples of perfluoropolyethers are:

$$CF_3\text{—}(C_3F_6O)_m\text{—}(CFXO)_n\text{—}CF_2Y \tag{1}$$

in which X and Y are a radical F or $CF_3$ and m and n are integers, the m/n ratio ranging from 5 to 40. These compounds and the method of preparing them are described in British Pat. No. 1,104,482.

$$C_3F_7O\text{—}(C_3F_6O)_m\text{—}Rf \tag{2}$$

in which Rf may be $C_2F_5$, $C_3F_7$, $CFHCF_3$, m is an integer higher than 2, preferably from 10 to 100. These compounds and the method of preparing them are described in the U.S. Pat. No. 3,242,218.

$$CF_3O(C_3F_6O)_m(C_2F_4O)_n(CFXO)_q\text{—}CF_3 \tag{3}$$

where $X=F$, $CF_3$ and m, n and q are integers; $m+n+q=10$–300; $n/q=0.5$–5; $m/q+n=0.01$–0.4. These compounds and the method of preparing them are described in U.S. Pat. No. 3,665,041.

$$CF_3O(C_2F_4O)_p(CF_2O)_q\text{—}CF_3 \tag{4}$$

where p and q are integers alike or different from each other and the p/q ratio ranges from 0.5 to 1.5. Examples of these compounds and the method of preparing them are described in U.S. Pat. Nos. 3,715,378 and 3,665,041. Examples of perfluoropolyethers containing polar end groups are described in U.S. Pat. No. 3,847,978 and in Italian Patent Application Nos. 21480 A/84 and 21481 A/84.

(5) The compounds having the oxetane structure are described in Italian Patent Application No. 19496 A/85.

(6) Perfluoropolyethers comprising $CF_2CF_2CF_2O$ units.

(7) Perfluoropolyethers comprising $CF_2CF_2O$ units.

The perfluoropolyethers of (6) and (7) are prepared respectively according to EP published application No. 148,482 (Daikin) and U.S. Pat. No. 4,523,039 (Lagow).

In addition to the neutral perfluoropolyethers indicated above, one may also use perfluoropolyethers with functionalized end groups such as those described for example in European patent application Nos. 165,649 and 165,650, U.S. Pat. No. 3,810,874, EP No. 148,482 (Daikin), EP No. 151,877 (3M) or in an Italian application No. 22929 A/85.

As already mentioned, the compositions of the present invention give rise to considerable film-forming effects; the liquid film obtained is transparent and permeable to gases. A significant proof of the waterproof effect is furnished by applying a cream according to the invention onto the hands and by successively washing the hands. After washing, the water slides away leaving the skin dry and particularly glossy.

Such, effect, contrary to what happens with other water-repellent creams, occurs also when washing is carried out with surfactants.

Thanks to the above-mentioned properties, the compositions of the present invention are particularly suited to applications in the field of cosmetics and of dermatology.

Examples of these applications are:

(a) as protective creams and barrier creams (handcreams, ointments (unguents), or pastes to prevent irritations or dermatitis due to contact; water-repellent creams for dermatitis caused by household surfactants or for occupational dermatitis);

(b) in paedocosmetics (child cosmetics) as protective creams or pastes for children, for example in the treatment or prevention of the milk crust of the skin or the scalp;

(c) as sun-products, where the waterproofing effect on the skin secures the permanence of the sunlight-filtering active components;

(d) as products agaisnt wrinkles and for decorative cosmetics, for example in foundation products, eye shadows, etc. In this case, the presence of the fluorinated compound promotes the flowability and therefore facilitates the spreading of the products, thus avoiding or minimizing the unaesthetic cakings (agglomerations) of the product on the skin; in lipsticks and lip-glosses, for example, an improvement in both flowability and glossiness is obtained;

(e) as creams for massages: since the perfluorinated compound is not absorbed by the skin, it permits also prolonged massages, allowing furthermore the penetration of active substances, if any;

(f) in dermatological applications, as a carrier for the absorption of drugs.

The perfluoropolyether content in the cosmetic emulsions varies as a function of the kind of use, of the number of daily applications, and of the application period. Generally it ranges from 0.5–1% for anti-wrinkle creams to be used every day up to 5–10% for high-protective creams. The persistence of the perfluoropolyether on the skin is rather long; the removal occurs by washing or by diffusion on clothes or by natural desquamation of the skin.

The following examples are given merely to illustrate and not to limit the scope of the invention.

EXAMPLE 1

Preparation of non-ionic O/W Emulsions

The preparation was carried out by using a SILVERSTON L2R mixing turbine.

As perfluoropolyethers there were utilized various types of FOMBLIN Y having the formula

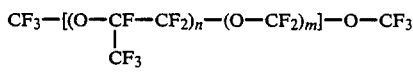

manufactured by Montefluos S.p.A : FOMBLIN Y04 (mean molecular weight 1,500 and viscosity 35 cSt at 20° C.), FOMBLIN Y25 (mean molecular weight 3,000 and viscosity 250 cSt at 20° C.), and FOMBLIN YR (mean molecular weight 6,000–7,000 and viscosity 1,000–2,000 cSt at 20° C.).

Except for slight variations in viscosity, no particular differences caused by the utilization of the three different types of FOMBLIN Y were observed in the final product.

The preparation was accomplished by emulsifying the Fomblin in water at 75° C. (SILVERSTON L2R mixing turbine at 6000 rpm).

Subsequently—while continuing to keep the mixing turbine running—the oily phase heated to 75° C. and containing the emulsifying agents, was added; finally, the preparation was completed under continuous and prolonged stirring.

The formula employed for preparing a series of creams was the following:

| | |
|---|---|
| water contained in the cream: | 76 parts |
| glycerine | 5 parts |
| fatty acids $C_{12}$–$C_{18}$ polyethoxylated with 8 molecules of ethylene oxide | 8 parts |
| fluid triglyceride | 4 parts |
| cetyl and stearyl alcohols | 7 parts |
| Fomblin Y, various types | 1–3–5 parts. |

The creams had a viscosity ranging from 2500 to 35000 cSt at 5 rpm (revolutions per minute). In spite of the not particularly high viscosity, the creams have proved to be stable in the accelerated ageing tests.

To increase the viscosity, the percentage of fat phase was raised:

| | |
|---|---|
| water contained in the cream | 70 parts |
| glycerine | 4 parts |
| fatty acids $C_{12}$–$C_{18}$ polyethoxylated with 8 ethylene oxide molecules | 8 parts |
| fluid triglyceride | 10 parts |
| cetyl and stearyl alcohols | 8 parts |
| Fomblin Y, various types | 1–3–5 parts. |

The viscosity of the emulsion was 9,000–10,000 cSt at 20° C. By addition of glyceryl monostearate the emulsion viscosity and glossiness was further improved; this permitted one also to reduce the concentration of the cetyl and stearyl alcohols.

Conversely, by using ethoxylated cetyl and stearyl alcohols it was possible to obtain highly stable emulsions:

| | |
|---|---|
| water contained in the emulsion | 76.5 parts |
| glycerine | 5 parts |
| cetyl and stearyl alcohols ethoxylated with 12 molecules of ethylene oxide | 3.5 parts |
| cetyl and stearyl alcohols | 15 parts |
| Fomblin Y, various types | 1–3–5 parts. |

EXAMPLE 2

Preparation of anionic O/W Emulsions

Following the procedure of Example 1, emulsions according to the following recipe were prepared:

| | |
|---|---|
| water contained in the emulsion | 85 parts |
| self-emulsifying glyceryl mono- and distearate | 10 parts |
| glycerine | 5 parts |
| Fomblin Y | 1–3–5 parts. |

The glyceryl mono- and distearate contained small amounts of alkaline stearates, which rendered the emulsifying agent anionic. The emulsions passed all the accelerated ageing tests, including a test in the centrifuge (30 minutes at 5000 rpm).

The addition of triglycerides to this type of emulsion resulted in a lower glossiness and a lower stability of the preparation.

EXAMPLE 3

Preparation of W/O Emulsions

The W/O emulsions show generally the tendency to be less stable than the O/W emulsions; however, the presence of Fomblin Y did not further destabilize the system.

For the tests, Arlacel 481 (HLB 4.5) (sorbitan sesquioleate) was utilized as an emulsifier:

| | |
|---|---|
| Arlacel 481 | 10 parts |
| liquid paraffin | 38 parts |
| beeswax | 2 parts |
| water contained in the emulsion | 45 parts |
| magnesium sulphate | 0.7 parts |
| glycerine | 4.3 parts |
| Fomblin, various types | 1–3–5 parts. |

EXAMPLE 4

Anhydrous Ointments and Pastes

An ointment based on triglycerides and hydogenated castor-oil was utilized.

The hydrogenated castor-oil exhibited a gelifying effect due to the fact that after melting and subsequent cooling, under stirring and in the presence of oils, it formed a solid reticulated structure, which imparted to the system a rheologic behavior similar to that of the emulsions.

Castor-oil doses below 15% proved unsuitable for preparing stable compositions.

| | |
|---|---|
| Hydrogenated castor-oil, m.p. 46° C. | 15% |
| fluid triglyceride | 80% |
| Fomblun Y25 | 5% |

The emulsion proved to be rather stable to thermostatic and to storage tests on shelves, but highly unstable to centrifugation (5000 rpm, 30 minutes).

A higher stability, also in the test in the centrifuge, was exhibited by the following preparation:

| | |
|---|---|
| hydrogenated castor-oil | 15% |
| fluid triglyceride | 77% |
| glyceryl monostearate | 3% |
| Fomblin Y25 | 5% |

On the guideline of the preceding formulas, pastes useful, e.g., in paedocosmetics (child cosmetics) were prepared:

| | |
|---|---|
| hydrogenated castor-oil | 10% |
| paraffin oil | 50% |
| zinc oxide | 20% |
| lanolin | 13% |
| glyceryl monostearate | 2% |
| Fomblin Y25 | 5% |

What is claimed is:

1. A composition comprising a perfluoropolyether liquid dispersed in an oil in water emulsion or in a water in oil emulsion, or in a solid phase suited to form a gel, said solid phase being suspended in a liquid organic phase, said composition containing from 0.05 to 30 parts of perfluoropolyether per 100 parts of the total sum of the other components.

2. A composition of claim 1, in which the oil in water emulsion is non-ionic or anionic and in which the water in oil emulsion is non-ionic.

3. An ointment or paste according to claim 1, in which the perfluoropolyether is dispersed in hydrogenated castor-oil suspended in a liquid triglyceride.

4. A composition according to claim 1 or 2 or 3, in which the perfluoropolyether liquid includes repeating units C$_2$F$_4$O and/or C$_3$F$_6$O or units C$_2$F$_4$O and CF$_2$O and optio or units C$_3$F$_6$O and units CFXO (X = radical F or CF$_3$) statistically distributed along the chain, or includes perfluorooxetane units.

5. A composition according to claim 4, in which the perfluoropolyether is selected from the class consisting of compounds having formulas:

$$CF_3O-(C_3F_6O)_m(CFXO)_n-CF_2Y \quad (a)$$

where Y is F or CF$_3$;
X is the same as Y;
m and n are integers;
the m/n ratio ranges from 5 to 40, and units C$_3$F$_6$O and CFXO are statistically distributed along the chain;

$$C_3F_7O(C_3F_6O)_m-RF \quad (b)$$

where Rf = C$_2$F$_5$, C$_3$F$_7$, CFHCF$_3$, and m is an integer;

$$CF_3O(C_3F_6O)_m(C_2F_4O)_n(CFXO)_q-CF_3 \quad (c)$$

where X = F or CF$_3$;
m, n and q are integers whose sum is between 10 and 300;
n/q = 0.5–5; m/q + m = 0.01–0.4; and the units C$_3$F$_6$O, and C$_2$F$_4$O and CFXO are statistically distributed along the chain;

$$CF_3O(C_2F_4O)_p(CF_2O)_q-CF_3 \quad (d)$$

where p and q are integers alike or different from each other and the p/q ratio ranges from 0.5 to 1.5 and the units are statistically distributed along the chain; and (e) perfluoropolyethers having an oxetane structure.

6. A composition according to claim 4, in which one or both end groups of the perfluoropolyether chain consist of polar groups or aromatic rings.

7. A composition according to claim 4, in which the mean number molecular weight of the perfluoropolyethers is higher than 500 and ranges preferably from 1,000 to 10,000.

8. A cosmetic or dermatologic composition comprising a perfluoropolyether liquid dispersed in an oil water emulsion or in a water in oil emulsion or in a solid phase suited to form a gel, said solid phase being suspended in a liquid organic phase, said composition containing from 0.05 to 30 parts of perfluoropolyether per 100 parts of the total sum of the other components.

9. A cosmetic or dermatologic composition according to claim 8, in which the oil in water emulsion is non-ionic or anionic and in which the water in oil emulsion is non-ionic.

10. A cosmetic or dermatologic composition according to claim 8, in which the perfluoropolyether liquid includes repeating units C$_2$F$_4$O and/or C$_3$F$_6$O or units C$_2$F$_4$O and CF$_2$O and optionally C$_3$F$_6$O, or units C$_3$F$_6$O and units CFXO (X = F or CF$_3$) statistically distributed along the chain, or includes perfluorooxetane units.

11. A cosmetic or dermatologic composition according to claim 8, 9 or 10 characterized in that the composition is a cream, an ointment or a paste.

12. A composition as defined in claim 1 wherein the perfluoroether repeating units of the perfluoropolyether are —CF$_2$CF$_2$CF$_2$O— units.

13. A composition as defined in claim 1 wherein the perfluoroether repeating units of the perfluoropolyether are —CF$_2$CF$_2$O— units.

14. A cosmetic or dermatologic composition as defined in claim 8 wherein the perfluoroether repeating units of the perfluoropolyether are —CF$_2$CF$_2$CF$_2$O— units.

15. A cosmetic or dermatologic composition as defined in claim 8 wherein the perfluoroether repeating units of the perfluoropolyether are —CF$_2$CF$_2$O— units.

* * * * *